(12) United States Patent
Hatakeyama

(10) Patent No.: US 10,172,584 B2
(45) Date of Patent: Jan. 8, 2019

(54) METHOD FOR GENERATING APPROXIMATE FUNCTION OF TOTAL MTF OF X-RAY IMAGE, BASED ON CONDITIONS FOR IMAGING WITH X-RAY

(71) Applicant: Norihito Hatakeyama, Osaka (JP)

(72) Inventor: Norihito Hatakeyama, Osaka (JP)

( * ) Notice: Subject to any disclaimer, the term of this patent is extended or adjusted under 35 U.S.C. 154(b) by 218 days.

(21) Appl. No.: 15/270,383

(22) Filed: Sep. 20, 2016

(65) Prior Publication Data
US 2017/0020477 A1    Jan. 26, 2017

Related U.S. Application Data

(63) Continuation-in-part of application No. 15/189,172, filed on Jun. 22, 2016.

(30) Foreign Application Priority Data

Jul. 23, 2015 (JP) .................................. 2015-146234

(51) Int. Cl.
*A61B 6/00* (2006.01)

(52) U.S. Cl.
CPC .............. *A61B 6/541* (2013.01); *A61B 6/547* (2013.01)

(58) Field of Classification Search
CPC ....... A61B 6/5211; A61B 6/467; A61B 6/461; A61B 6/541; A61B 6/547; A61B 6/4233; G06T 5/002
See application file for complete search history.

(56) References Cited

U.S. PATENT DOCUMENTS 5,848,123 A    12/1998  Strömmer
2017/0020477 A1 *  1/2017  Hatakeyama .......... A61B 6/541

FOREIGN PATENT DOCUMENTS

JP    9-200625    7/1997

OTHER PUBLICATIONS

Fujita et al. "A Simple Method for Determining the Modulation Transfer Function in Digital Radiography," IEEE Transactions on Medical Imaging (1992) (Year: 1992).*
Zhou et al., "A Novel Method for MTF Measurement of Digital Radiographic Systems," 4th International Conference on Biomedical Engineering and Informatics (2011) (Year: 2011).*
Masaru Uchida et al., "Hoshasen gijutsusha no tame no gazo kogaku (Imaging Technology for Radiologists)", Tsusho Sangyo Kenkyu sha, co., 1978, pp. 48-51, pp. 178-179, with partial English translation.
(Continued)

*Primary Examiner* — Courtney D Thomas
(74) *Attorney, Agent, or Firm* — Wenderoth, Lind & Ponack, L.L.P.

(57) ABSTRACT

A method for generating approximate functions of total MTFs of x-ray images, based on conditions for imaging with an x-ray emitted by an x-ray tube, includes: a first generating step of generating an approximate function of an MTF based on an x-ray tube effective focal spot value on an object plane; a second generating step of generating an approximate function of an MTF based on the kind of an x-ray detector system on the object plane; a third generating step of generating an approximate function of an MTF based on the amount of motion of an object; and a fourth generating step of generating an approximate function of a total MTF.

3 Claims, 7 Drawing Sheets

(56) References Cited

OTHER PUBLICATIONS

Takashi Wakamatsu et al., "Shinryo hoshasen gijutsu—Jokan (Medical radiology technique—vol. 1)", fifth revision, Nankodo, 1985, pp. 320-321, with partial English translation.

Hiroshi Fujita et al., "Shinryo hoshasen gijutsu—Jokan (Medical radiology technique—vol. 1)", thirteenth revision, Nankodo, 2013, pp. 111-113, with partial English translation.

Hisatoshi Aoki and Hiroshi Yasuhara in Medical Equipment Division of Toshiba Corporation, "[Paper 69-4] I. I Kansetsu satsuei no gashitsu hyoka (Image quality evaluation in indirect imaging)", J-Stage (online), vol. 11, No. 3, 1981, pp. 103-105, with partial English translation.

Masao Matsumoto et al., "Evaluation of Radiographic Image Qualities Including Object Motion by Information Spectra", Journal No. 3 of vol. 54 of the Society of Photography and Imaging of Japan, 1991, pp. 335-340, with partial English.

\* cited by examiner

FIG. 4

| | Nominal focal spot value | Tube voltage | Tube current | Imaging time | SID | SOD |
|---|---|---|---|---|---|---|
| Imaging condition combination 1 | 0.6 mm | 120 kVp | 100 mA | 0.032 s | 200 cm | 188 cm |
| Imaging condition combination 2 | 1.2 mm | 120 kVp | 200 mA | 0.016 s | 200 cm | 188 cm |
| Imaging condition combination 3 | 1.2 mm | 100 kVp | 320 mA | 0.028 s | 200 cm | 188 cm |
| Imaging condition combination 4 | 1.2 mm | 100 kVp | 320 mA | 0.014 s | 140 cm | 128 cm |

FIG. 5

| Tube voltage [kVp] | Tube current [mA] (Nominal focal spot value 0.6 mm) | | | | Tube current [mA] (Nominal focal spot value 1.2 mm) | | | | | | | | |
|---|---|---|---|---|---|---|---|---|---|---|---|---|---|
| | 50 | | 100 | | 160 | | 200 | | 250 | | 320 | | |
| | f1 | f2 | f1 | f2 | f1 | f2 | f1 | f2 | f1 | f2 | f1 | f2 | |
| 40-42 | 0.72 | 2.1 | 0.9 | 2.1 | 1.5 | 2.1 | 1.55 | 2.1 | 1.6 | 2.1 | 1.64 | 2.1 | |
| 43-47 | 0.67 | 2.1 | 0.85 | 2.1 | 1.45 | 2.1 | 1.49 | 2.1 | 1.54 | 2.1 | 1.58 | 2.1 | |
| 48-52 | 0.63 | 2.1 | 0.8 | 2.1 | 1.4 | 2.1 | 1.44 | 2.1 | 1.48 | 2.1 | 1.51 | 2.1 | |
| 53-57 | 0.58 | 2.1 | 0.75 | 2.1 | 1.35 | 2.1 | 1.38 | 2.1 | 1.42 | 2.1 | 1.45 | 2.1 | |
| 58-62 | 0.54 | 2.1 | 0.7 | 2.1 | 1.3 | 2.1 | 1.33 | 2.1 | 1.36 | 2.1 | 1.39 | 2.1 | |
| ... | ... | ... | ... | ... | ... | ... | ... | ... | ... | ... | ... | ... | |
| 93-97 | 0.62 | 2.1 | 0.71 | 2.1 | 1.36 | 2.1 | 1.41 | 2.1 | 1.44 | 2.1 | 1.52 | 2.1 | |
| 98-102 | 0.61 | 2.1 | 0.7 | 2.1 | 1.35 | 2.1 | 1.4 | 2.1 | 1.45 | 2.1 | 1.5 | 2.1 | |
| ... | ... | ... | ... | ... | ... | ... | ... | ... | ... | ... | ... | ... | |

FIG. 6

| Kind of x-ray detector system | S1 | S2 |
|---|---|---|
| Flat panel | 0.085 | 2 |
| CR1 | 0.095 | 2 |
| CR2 | 0.095 | 2.4 |

FIG. 7

| Object | Maximum amount of motion [mm] | Time required to reach maximum amount of motion [s] |
|---|---|---|
| Breast part (around periphery of heart) | 10 | 0.4 |
| Breast part (around hilum of left lung) | 3 | 0.4 |
| Abdominal part (around stomach and intestines) | 20 | 20 (Normal state) |
| | | 7 (Diarrhea state) |
| | | 3 (State after intake of barium) |

FIG. 8

| | M | f1 | f2 | S1 | S2 | d |
|---|---|---|---|---|---|---|
| Imaging condition combination 1 | 1.064 | 0.63 | 2.1 | 0.085 | 2.0 | 0.24 |
| Imaging condition combination 2 | 1.064 | 1.35 | 2.1 | 0.085 | 2.0 | 0.12 |
| Imaging condition combination 3 | 1.064 | 1.5 | 2.1 | 0.085 | 2.0 | 0.21 |
| Imaging condition combination 4 | 1.094 | 1.5 | 2.1 | 0.085 | 2.0 | 0.105 |

METHOD FOR GENERATING APPROXIMATE FUNCTION OF TOTAL MTF OF X-RAY IMAGE, BASED ON CONDITIONS FOR IMAGING WITH X-RAY

CROSS REFERENCE TO RELATED APPLICATIONS

The present application is a continuation-in-part of U.S. application Ser. No. 15/189,172, filed on Jun. 22, 2016, and claims the benefit of Japanese Patent Application No. 2015-146234 filed on Jul. 23, 2015. The entire disclosures of the above-identified applications, including the specifications, drawings and claims are incorporated herein by reference in their entireties.

FIELD

The present invention relates to a method for generating an approximate function of a total modulation transfer function (MTF) indicating a resolution characteristic of an x-ray image, based on conditions for imaging with an x-ray emitted by an x-ray tube.

BACKGROUND

In the formation of an x-ray image (hereinafter also referred to as an image) of an object which is a predetermined part (for example, the breast part or abdominal part of a human body with a motion), there are a plurality of x-ray imaging condition combinations (hereinafter also referred to as imaging condition combinations) which provide equivalent analog photograph concentrations (hereinafter also referred to as equivalent concentrations) or equivalent digital exposure index (EI) values (hereinafter also referred to as equivalent EI values). Each of the plurality of imaging condition combinations includes, for example, the distance between an x-ray tube focal plane and an x-ray detector system plane, the distance between the x-ray tube focal plane and an object plane, an x-ray tube nominal focal spot value, a tube voltage, a tube current, imaging time, and the kind of an x-ray detector system.

When imaging an object of a human body with a motion, it is difficult to predict an imaging condition combination which enables obtainment of a high-resolution Image in a short period of time.

Currently, as an example of a method for predicting an imaging condition combination which enables obtainment of a high-resolution image, there is a method for imaging test charts with a motion under different imaging condition combinations, and comparing the resolutions of the resulting images by means of visual check. However, this method requires extremely long time to perform tests on all of the imaging condition combinations. In addition, since the resolutions are compared by means of visual check by humans, there are cases where the resolutions are not compared accurately.

As another example of a method for predicting an imaging condition combination which enables obtainment of a high-resolution image, there is a method for comparing resolution characteristics (MTFs). This method focuses on total MTFs each generated based on three major elements which blur an image. The total MTF is an MTF obtained by multiplying an MTF based on an x-ray tube effective focal spot value, an MTF based on the amount of motion of the object, and an MTF based on the kind of the x-ray detector system.

Non-patent Literatures 1 to 4 disclose techniques related to such MTFs.

More specifically, Non-patent Literatures 1 to 4 disclose examples of approximate functions of MTFs based on the kinds of x-ray detector systems as blurring elements. Non-patent Literatures 1 to 4 further disclose examples of approximate functions of MTFs based on the amount of motion of objects as blurring elements. Non-patent Literatures 1 to 4 further disclose examples of approximate functions of MTFs based on x-ray tube nominal focal spot values as blurring elements. Furthermore, Non-patent Literatures 1 to 4 disclose that approximate functions of total MTFs are generated by multiplying approximate functions of MTFs based on x-ray tube nominal focal spot values and approximate functions of MTFs based on the kind of the x-ray detector systems, and that simulation is performed based on approximate functions of the total MTFs. In this way, the approximate functions of the total MTFs are generated for respective imaging condition combinations through a fast operation process by a computer or the like in a short period of time. By means of the approximate functions of the total MTFs are generated for the respective imaging condition combinations being expressed using numerical values or a graph, it is possible to compare the differences in resolution characteristics due to the differences in the imaging condition combinations.

CITATION LIST

Non Patent Literature

[NPL 1]
  Masaru Uchida, Kazuya Yamashita, and Hiroshi Inatsu, "*Hoshasen gijutsusha no tame no gazo kogaku* (Imaging technology for radiologists", *Tsusho Sangyo Kenkyu sha*, co. 1978
[NPL 2]
  Takashi Wakamatsu, Kazuo Sugumi, and Kazuya Yamashita, "*Shinryo hoshasen gijutsu—Jokan* (Medical radiology technique—volume 1)", fifth revision, Nankodo, 1985
[NPL 3]
  Hiroshi Fujita, Kazuya Yamashita, Takayuki Ishida, and Kiyonari Inamura, "*Shinryo hoshasen gijutsu—Jokan* (Medical radiology technique—volume 1)", thirteenth revision, Nankodo, 2013
[NPL 4]
  Hisatoshi Aoki, and Hiroshi Yasuhara in Medical Equipment Division of Toshiba Corporation, "[Paper 69-4] I. I *Kansetsu satsuei no gashitsu hyoka* (Image quality evaluation in indirect imaging)", J-STAGE (online), vol. 11 no. 3, 1981

SUMMARY

Technical Problem

However, none of Non-patent Literatures 1 to 4 discloses a method for determining numerical values that should be input to approximate functions of the respective elements which cause blurs. Stated differently, since none of them disclose a method for generating approximate functions of the respective elements which cause blurs, it is difficult to generate an approximate function of a total MTF. In addition, the x-ray tube nominal focal spot value and the x-ray tube effective focal spot value are slightly different from each other.

In view of this, the present invention provides a method for generating, based on conditions for imaging with an x-ray emitted by an x-ray tube, an approximate function of a total MTF of an x-ray image which makes it possible to easily compare the differences in resolution characteristics due to the differences in imaging condition combinations.

Solution to Problem

A method for generating an approximate function of a total modulation transfer function (MTF) of an x-ray image of an object, based on conditions for imaging with an x-ray emitted by an x-ray tube, the total MTF indicating a resolution characteristic of the x-ray image, the x-ray image being obtained by imaging the object which is a predetermined part of a human body with a motion, the method comprising:

an obtaining step of obtaining imaging condition combinations for the x-ray and conditions for the human body at a time of imaging, the imaging condition combinations including a magnification ratio obtained by dividing a distance between an x-ray tube focal plane and an x-ray detector system plane by a distance between the x-ray tube focal plane and an object plane, an x-ray tube nominal focal spot value, a tube voltage, a tube current, imaging time, and a kind of an x-ray detector system, the conditions for the human body including a kind of the object, a state of the object, a maximum amount of motion of the human body, and time required for an amount of motion of the human body to reach the maximum amount of motion of the human body;

a first generating step of (i) generating an approximate function of an MTF based on an x-ray tube effective focal spot value on the x-ray tube focal plane by checking an imaging condition combination of the x-ray tube nominal focal spot value, the tube voltage, and the tube current among the imaging condition combinations obtained in the obtaining step, against a predefined first correspondence relation between the imaging condition combination of the x-ray tube nominal focal spot value, the tube voltage, and the tube current and values in the approximate function of the MTF based on the x-ray tube effective focal spot value on the x-ray tube focal plane, and (ii) converting, using the magnification ratio, the approximate function generated into an approximate function of an MTF based on the x-ray tube effective focal spot value on the object plane;

a second generating step of (i) generating an approximate function of an MTF based on the kind of an x-ray detector system on the x-ray detector system plane by checking the kind of the x-ray detector system among the imaging condition combinations obtained in the obtaining step, against a predefined second correspondence relation between the kind of the x-ray detector system and values in the approximate function of the MTF based on the kind of the x-ray detector system on the x-ray detector system plane, and (ii) converting, using the magnification ratio, the approximate function generated into an approximate function of an MTF based on the kind of the x-ray detector system on the object plane;

a third generating step of generating an approximate function of an MTF based on an amount of motion of the object, the amount of motion of the object being determined by: (a) a maximum amount of motion made by an organ in the object, (b) time required for an amount of motion made by the organ in the object to reach the maximum amount of motion made by the organ in the object, (c) the imaging time, (d) the maximum amount of motion of the human body, and (e) the time required for the amount of motion of the human body to reach the maximum amount of motion of the human body, (a) the maximum amount of motion made by an organ in the object and (b) the time required for an amount of motion made by the organ in the object to reach the maximum amount of motion made by the organ in the object being obtained by checking the kind of the object and the state of the object obtained in the obtaining step against a predefined third correspondence relation between (i) the kind of the object and the state of the object and (ii) the maximum amount of motion made by the organ in the object and the time required for the amount of motion made by the organ in the object to reach the maximum amount of motion made by the organ in the object; and a fourth generating step of generating an approximate function of a total MTF by multiplying the approximate function of the MTF based on the x-ray tube effective focal spot value on the object plane, the approximate function of the MTF based on the kind of the x-ray detector system on the object plane, and the approximate function based on the amount of motion of the object on the object plane, wherein values in the approximate function of the MTF based on the x-ray tube effective focal spot value on the x-ray tube focal plane in the first correspondence relation are values predetermined for each imaging condition combination of the x-ray tube nominal focal spot value, the tube voltage, and the tube current, so that a function which indicates the MTF based on the x-ray tube effective focal spot value on the x-ray tube focal plane approximates to a measured MTF based on the x-ray tube effective focal spot value for each imaging condition combination of the x-ray tube nominal focal spot value, the tube voltage, and the tube current on the x-ray tube focal plane in a spatial frequency domain on the x-ray tube focal plane calculated by setting the magnification ratio to be a value within a predetermined range and setting a spatial frequency domain which has a spatial frequency on the object plane to be a predetermined spatial frequency domain, values in the approximate function of the MTF based on the kind of the x-ray detector system on the x-ray detector system plane in the second correspondence relation are values predetermined for each kind of the x-ray detector system, so that a function which indicates the MTF based on the kind of the x-ray detector system on the x-ray detector system plane approximates to a measured MTF for each kind of the x-ray detector system on the x-ray detector system plane in a spatial frequency domain on the x-ray detector system plane calculated by setting the magnification ratio to be a value within a predetermined range and setting a spatial frequency domain which has a spatial frequency on the object plane to be a predetermined spatial frequency domain, and the amount of motion of the object is:

an amount of motion expressed as a product of the imaging time and a sum of an amount of motion of the human body per second and an amount of motion made by the organ per second when time required for the amount of motion of the human body to reach a maximum amount of motion of the human body is longer than the imaging time and time required for the amount of motion made by the organ to reach a maximum amount of motion made by the organ is longer than the imaging time;

an amount of motion expressed as a sum of (i) a product of the imaging time and an amount of motion of the human body per second and (ii) a maximum amount of motion made by the organ when time required for the amount of motion of the human body to reach a maximum amount of motion of the human body is longer than the imaging time and time required for the amount of motion made by the organ to reach a maximum amount of motion made by the organ is shorter than the imaging time;

an amount of motion expressed as a sum of (i) a maximum amount of motion of the human body and (ii) a product of the imaging time and an amount of motion made by the organ per second when time required for the amount of motion of the human body to reach a maximum amount of motion of the human body is shorter than the imaging time and time required for the amount of motion made by the organ to reach a maximum amount of motion made by the organ is longer than the imaging time; and an amount of motion expressed as a sum of a maximum amount of motion of the human body and a maximum amount of motion made by the organ when time required for the amount of motion of the human body to reach a maximum amount of motion of the human body is shorter than the imaging time and time required for the amount of motion made by the organ to reach a maximum amount of motion made by the organ is shorter than the imaging time.

Advantageous Effects

The method for generating, based on conditions for imaging with an x-ray emitted by an x-ray tube, an approximate function of a total MTF of an x-ray image according to an aspect of the present invention makes it possible to easily compare the differences in resolution characteristics due to the differences in imaging condition combinations.

BRIEF DESCRIPTION OF DRAWINGS

These and other objects, advantages and features of the invention will become apparent from the following description thereof taken in conjunction with the accompanying drawings that illustrate a specific embodiment of the present invention.

FIG. 4 is a diagram illustrating examples of imaging condition combinations each of which is for the case where an obtaining unit according to the embodiment obtains an image which has an equivalent concentration or an equivalent EI value.

FIG. 5 is a diagram illustrating examples of first correspondence relations.

FIG. 6 is a diagram illustrating examples of second correspondence relations.

FIG. 7 is a diagram illustrating examples of third correspondence relations.

FIG. 8 is a diagram illustrating examples of values in approximate functions of total MTFs.

DESCRIPTION OF EMBODIMENTS

Hereinafter, methods according to embodiments of the present invention are described with reference to the drawings. It is to be noted that each of the embodiments below describes a preferred example of the present invention. Accordingly, the numerical values, constituent elements, the arrangement of the constituent elements, connection states, steps, the order of the steps, etc. illustrated in the embodiments below are examples, and thus are not intended to limit the present invention. Thus, among the constituent elements of the embodiments below, constituent elements which are not described in the independent claim which indicates the most generic concept of the present invention are described as arbitrary constituent elements.

In addition, each of the drawings is a schematic diagram, and thus is not always illustrated precisely.

Embodiment

[X-Ray System]

Figure 1:
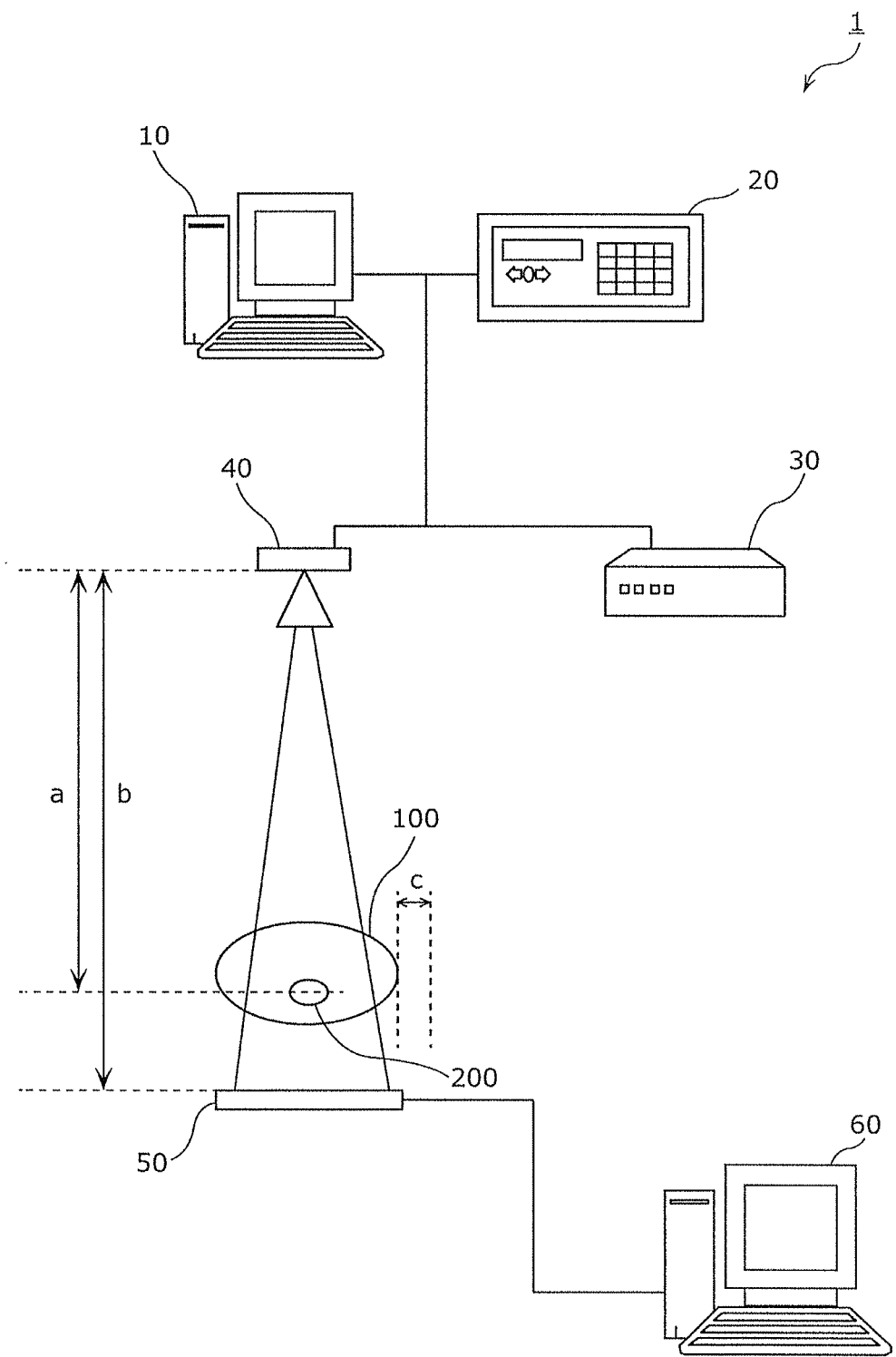
FIG. 1 is a diagram illustrating an overall configuration of an x-ray system according to an embodiment.

FIG. 1 is a diagram illustrating an overall configuration of an x-ray system 1 according to an embodiment.

The x-ray system 1 is a system for obtaining an x-ray image of an object, and includes a computer 10, an operation panel 20, a high-voltage generating device 30, an x-ray tube 40, an x-ray detector system 50, and a display device 60. FIG. 1 also illustrates a human body 100 and an object (test target part) 200 which is a predetermined part in the human body 100.

The computer 10 executes a program for generating approximate functions of total MTFs. More specifically, the computer 10 executes the program for generating an approximate function of a total MTF for each of imaging condition combinations through a fast operation process in a short period of time, and displaying, for each imaging condition combination, the approximate function of the total MTF as simulation data expressed using numerical values or a graph so that resolutions of x-ray images under the respective image condition combinations can be compared with each other. Operations performed by the computer 10 are described in detail later with reference to FIGS. 2 and 3.

The operation panel 20 is a panel for receiving operations by an imaging person, and receives, for example, a plurality of imaging condition combinations. Each of the imaging condition combinations includes: the distance a between the focal plane of the x-ray tube 40 (hereinafter referred to as an x-ray tube focal plane) and an object 200 plane; the distance b between the x-ray tube focal plane and an x-ray detector system 50 plane; an x-ray tube nominal focal spot value, a tube voltage, a tube current, imaging time, and the kind of an x-ray detector system 50 to be used. In addition, the operation panel 20 receives conditions for human body 100 at the time of imaging. For example, the conditions include: the kind of the object 200 (for example, a breast part, an abdominal part, or the like); the state of the object 200 (for example, a normal state, a diarrhea state, a state after intake of barium, or the like in the case where the object 200 is the abdominal part); the maximum amount c of motion of the human body 100 taken for example by the imaging person; and time required for the amount of motion of the human body 100 to reach the maximum amount c of motion of the human body 100. It is to be noted that the operation panel 20 may include a display unit which displays information received by the operation panel 20. In addition, the operation panel 20 may be included in the computer 10, and a display unit included in the computer 10 may display the information received by the operation panel 20.

The high-voltage generating device 30 is a device for supplying a high current of a high voltage to the x-ray tube 40. For example, the high-voltage generating device 30 supplies, to the x-ray tube 40, a tube voltage and a tube current suitable for an imaging condition combination corresponding to simulation data compared and selected by the imaging person.

The x-ray tube 40 is a device for irradiating an x-ray suitable for the tube voltage and the tube current to be supplied from the high-voltage generating device 30. For example, the x-ray tube 40 provides two focal spots which are a small focal spot (which has a nominal focal spot value of 0.6 mm) and a large focal spot (which has a nominal focal spot value of 1.2 mm). The small focal spot and large focal spot are switched depending on applications. For example, the large focal spot is used when a large tube current (for example, 160 to 400 mA) is to be supplied, and the small focal spot is used when a small tube current (for example, 50 to 100 mA) is to be supplied. Accordingly, the operation panel 20 may not receive, as one of the imaging condition combinations, an imaging condition combination including a large tube current and a small focal spot or an imaging condition combination including a small tube current and a large focal spot.

The x-ray detector system 50 detects the human body 100 and x-ray transmitted through the object 200. In the case of an analog x-ray detector system, the x-ray detector system 50 is a combination of a film and an intensifying screen for example. In the case of a digital x-ray detector system, the x-ray detector system 50 is a flat panel detector, a computed radiography device, or the like.

The display device 60 is a display device which displays an x-ray image detected by the x-ray detector system 50. It is to be noted that the display unit of the computer 10 may display the x-ray image detected by the x-ray detector system 50.

Here, the distance a is a source-object distance (SOD) between the x-ray tube focal plane and the object 200 plane. The distance b is a source-image distance (SID) between the x-ray tube focal plane and the x-ray detector system 50 plane. The distance c is the maximum amount of motion of the human body 100 on the object plane perpendicular to the incident direction of the x-ray. For example, the x-ray system 1 may include a position detecting sensor, and thereby measure the distances a and b. In addition, the computer 10 may automatically calculate a magnification ratio to be described later, according to the distances a and b detected by the position detecting sensor.

[Operations by Computer]

Next, operations performed by the computer 10 are described with reference to FIGS. 2 and 3.

Figure 2:
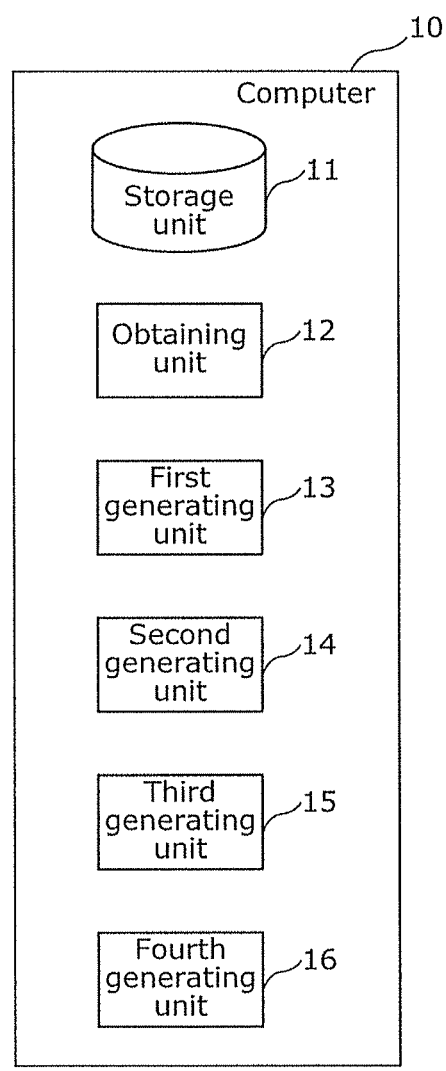
FIG. 2 is a block diagram illustrating examples of functions of a computer according to the embodiment.

FIG. 2 is a block diagram illustrating examples of functions of the computer 10 according to this embodiment.

Figure 3:
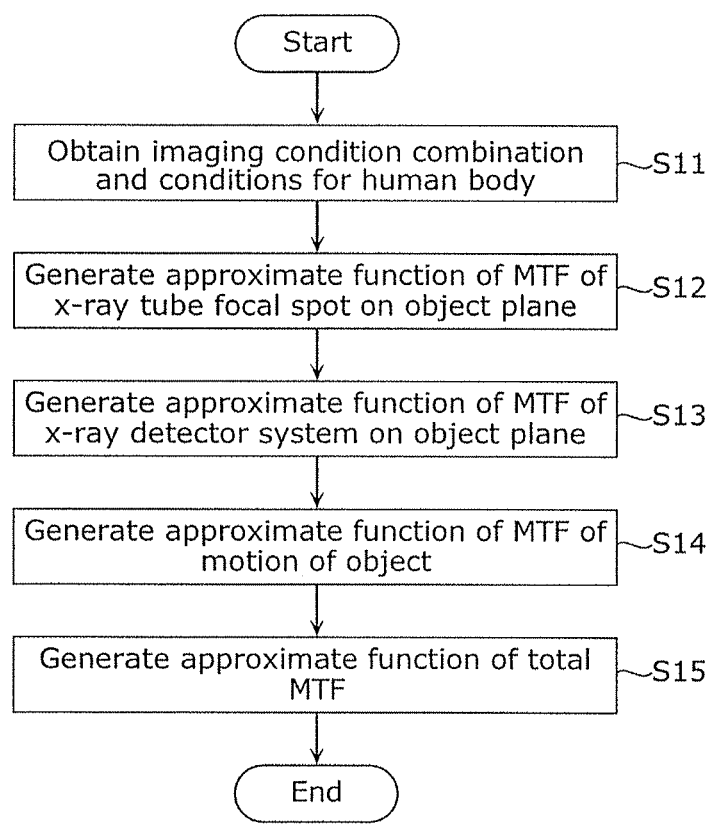
FIG. 3 is a flowchart indicating examples of operations performed by the computer according to the embodiment.

FIG. 3 is a flowchart indicating examples of operations performed by the computer 10 according to this embodiment.

The computer 10 includes a storage unit 11, an obtaining unit 12, a first generating unit 13, a second generating unit 14, a third generating unit 15, and a fourth generating unit 16. The computer 10 includes a processor for example. The obtaining unit 12, the first generating unit 13, the second generating unit 14, the third generating unit 15, and the fourth generating unit 16 are configured in the form of, for example, a processor which executes a control program stored in the storage unit 11, but may be configured using a microcomputer, an exclusive circuit, or the like.

The storage unit 11 stores a program for the execution by the computer 10 and a database for converting an imaging condition combination and conditions for the human body 100 obtained by the obtaining unit 12 to be described later to an approximate function. The database indicates first correspondence relations, second correspondence relations, and third correspondence relations to be described later with reference to FIGS. 5, 6, and 7. Specific operations by the computer 10 are performed by the obtaining unit 12, the first generating unit 13, the second generating unit 14, the third generating unit 15, and the fourth generating unit 16.

The obtaining unit 12 obtains an imaging condition combination including: a magnification ratio obtained by dividing the distance between an x-ray tube focal plane and an x-ray detector system 50 plane by the distance between the x-ray tube focal plane and an object 200 plane; an x-ray tube nominal focal spot value; a tube voltage; a tube current; and imaging time; and the kind of an x-ray detector system 50 (Step S11), and conditions for the human body 100 including: the kind of the object 200; the state of the object 200; the maximum amount c of motion of the human body 100; and time required for the amount of motion of the human body 100 to reach the maximum amount c of motion of the human body 100.

The imaging condition combination is composed of imaging conditions in the case where an image which has an equivalent concentration or an equivalent EI value is obtained when imaging an object 200 with a motion. The imaging person inputs the plurality of imaging condition combinations to an operation panel 20. The obtaining unit 12 obtains information indicating the plurality of imaging condition combinations through the operation panel 20. The imaging condition combinations are described in detail later with reference to FIG. 4. The kind of the object 200 is, for example, a breast part, an abdominal part, or the like. In the case where an imaging target is the breast part, the kind of the object 200 is the breast part. In the case where an imaging target is the abdominal part, the state of the object 200 is, for example, a normal state, a diarrhea state, a state after intake of barium, or the like. The maximum amount c of motion of the human body 100 is, for example, the maximum amount of motion such as swing of the human body 100. The time required for the amount of motion of the human body 100 to reach the maximum amount c of motion of the human body 100 is, for example, time required for the amount of motion such as swing of the human body 100 to reach the maximum amount c of motion of the human body 100.

The first generating unit 13 generates an approximate function of an MTF based on an x-ray tube effective focal spot value on the object 200 plane (Step S12). More specifically, the first generating unit 13 generates an approximate function of an MTF based on an x-ray tube effective focal spot value on the x-ray tube focal plane by checking the imaging condition combination of the x-ray tube nominal focal spot value, the tube voltage, and the tube current among the imaging condition combinations obtained by the obtaining unit 12, against a predefined first correspondence relation between the imaging condition combination of the x-ray tube nominal focal spot value, the tube voltage, and the tube current, and values in the approximate function of the MTF based on the x-ray tube effective focal spot value on the x-ray tube focal plane. The first generating unit 13 next converts the approximate function to an approximate function of an MTF based on an x-ray tube effective focal spot value on the object 200 plane using the magnification ratio. First correspondence relations are described in detail later with reference to FIG. 5.

The second generating unit 14 generates an approximate function of an MTF based on the kind of an x-ray detector system 50 on the object 200 plane (Step S13). More specifically, the second generating unit 14 generates an approximate function of an MTF based on the kind of an x-ray detector system 50 on the x-ray detector system 50 plane by checking the kind of the x-ray detector system 50 in one of the imaging condition combinations obtained by the obtaining unit 12, against a predefined second correspondence relation between the kind of the x-ray detector system 50 and values in the approximate function of the MTF based on the kind of the x-ray detector system 50 on the x-ray detector system plane. The second generating unit 14 next converts the approximate function to an approximate function of an MTF based on the kind of an x-ray detector system 50 on the object 200 plane using the magnification ratio. Second correspondence relations are described in detail later with reference to FIG. 6.

The third generating unit 15 generates an approximate function of an MTF based on the amount of motion of the object 200 on the object 200 plane (Step S14). More specifically, the third generating unit 15 generates an approximate function of an MTF based on the amount of motion of the object 200 which includes the amount of motion of the human body 100 and the amount of motion made by an organ in the object 200 on the object 200 plane in imaging time in one of the imaging condition combinations obtained by the obtaining unit 12. Each of the third correspondence relations is a correspondence relation between (i) the kind of the object 200 and the state of the object 200 and (ii) the maximum amount of motion made by an organ in the object 200 and time required for the amount of motion made by the organ to reach the maximum amount of motion made by the organ. The third correspondence relations are described in detail later with reference to FIG. 7. In addition, details of a method for determining the amount of motion of the object 200 is described later. It is to be noted that the order of operations in Steps S12 to S14 is not limited to this, and any other order is possible.

The fourth generating unit 16 generates an approximate function of a total MTF (Step S15). More specifically, the fourth generating unit 16 generates an approximate function of a total MTF by multiplying the following: the approximate function of the MTF based on the x-ray tube effective focal spot value on the object 200 plane; the approximate function of the MTF based on the kind of the x-ray detector system 50 on the object 200 plane; and the approximate function based on the amount of motion of the object 200 on the object 200 plane.

Here, descriptions are given of the approximate function of the MTF based on the x-ray tube effective focal spot value on the object 200 plane, the approximate function of the MTF based on the amount of motion of the object 200 on the object 200 plane, the approximate function of the MTF based on the kind of the x-ray detector system 50 on the object 200 plane, and the approximate function of the total MTF.

The x-ray tube effective focal spot value, the amount of motion of the object 200, and the kind of the x-ray detector system 50 are three major elements that blur an x-ray image. Here, for example, it is assumed that the MTF based on the x-ray tube effective focal spot value on the x-ray tube focal plane is a function G (u1), the MTF based on the amount of motion of the object 200 on the object 200 plane is a function T (u), and that the MTF based on the kind of the x-ray detector system 50 on the x-ray detector system plane is a function E (u2). The MTF obtained by multiplying these functions is a total MTF, and, for example, is expressed as a TMTF (u) according to Expression 1 below.

$$TMTF(u) = |G(u1) \times T(u) \times E(u2)| \quad \text{(Expression 1)}$$

Here, u denotes a spatial frequency (cycles/mm) on the object 200 plane, u1 denotes a spatial frequency on the x-ray tube focal plane, and u2 denotes a spatial frequency on the x-ray detector system 50 plane. The approximate functions thereof have been normalized.

The function G (u1) developed for indicating the MTF based on the x-ray tube effective focal spot value on the x-ray tube focal plane which is a plane perpendicular to the incident direction of the x-ray is expressed by Expression 2 below.

$$G(u1) = \exp\left(-2\pi^2 \left(\frac{(f1)}{3}\right)^2 (u1)^{(f2)}\right) \quad \text{(Expression 2)}$$

Here, f1 and f2 are values which are based on an imaging condition combination of an x-ray tube nominal focal spot value, a tube voltage, and a tube current, and are in an approximate function of the MTF based on the x-ray tube effective focal spot value on the x-ray tube focal plane which is a plane perpendicular to the incident direction of the x-ray. These f1 and f2 are described in detail later.

Expression 3 below shows the function T (u) developed for indicating the MTF based on the amount of motion of the object 200 on the object 200 plane which is a plane perpendicular to the incident direction of the x-ray.

$$T(u) = \frac{\sin(\pi u d)}{\pi u d} \quad \text{(Expression 3)}$$

Here, u denotes a spatial frequency in the object 200 plane (which is the perpendicular plane including the object 200 with respect to the incident direction of the x-ray). In addition, d denotes the amount of motion (mm) of the object 200 on the object 200 plane in imaging time, and is described in detail later.

Expression 4 below shows the function E (u2) developed for indicating the MTF based on the kind of the x-ray detector system 50 on the x-ray detector system 50 plane which is a plane perpendicular to the incident direction of the x-ray.

$$E(u2) = \frac{1}{1 + 4\pi^2 (S1)^2 (u2)^{(S2)}} \quad \text{(Expression 4)}$$

Here, S1 and S2 are values which are based on the kind of the x-ray detector system 50, and are in an approximate function of the MTF based on the kind of the x-ray detector system 50 on the x-ray detector system 50 plane. These S1 and S2 are described in detail later.

The MTF based on the x-ray tube effective focal spot value expressed by Expression 2 is an MTF on the x-ray tube focal plane, and the MTF based on the kind of the x-ray detector system 50 expressed by Expression 4 is an MTF on the x-ray detector system 50 plane. Stated differently, in order to multiply these MTFs, there is a need to convert the spatial frequencies to spatial frequencies on the object 200 plane. For this reason, each of the MTF based on the x-ray tube effective focal spot value on the x-ray tube focal plane and the MTF based on the kind of the x-ray detector system 50 on the x-ray detector system 50 plane is converted to an MTF on the object 200 plane using the magnification ratio M.

A function G (u) developed for indicating the MTF based on the x-ray tube effective focal spot value on the object 200 plane is expressed by Expression 5 below.

$$G(u) = \exp\left(-2\pi^2 \left(\frac{f1}{3}\right)^2 \left(\left(\frac{(M-1)}{M}\right)u\right)^{(f2)}\right) \quad \text{(Expression 5)}$$

The function E (u) developed for indicating the MTF based on the kind of the x-ray detector system 50 on the object 200 plane is expressed by Expression 6 below.

$$E(u) = \frac{1}{1 + 4\pi^2 (S1)^2 \left(\frac{1}{M}u\right)^{(S2)}} \quad \text{(Expression 6)}$$

The magnification ratio M is expressed by Expression 7 below.

$$M = \frac{b}{a} \quad \text{(Expression 7)}$$

Here, a and b denote distances a and b illustrated in FIG. 1 described earlier.

Based on these expressions, the function TMTF (u) indicating the total MTF is expressed by Expression 8 below.

$$TMTF(u) = |G(u) \times T(u) \times E(u)| \quad \text{(Expression 8)}$$

In addition, imaging condition combinations each of which is for the case where an image which has an equivalent concentration or an equivalent EI value is obtained by the obtaining unit 12 in Step S11 are described with reference to FIG. 4.

FIG. 4 is a diagram illustrating examples of imaging condition combinations each of which is for the case where an obtaining unit 12 according to the embodiment obtains the image which has the equivalent concentration or the equivalent EI value. It is to be noted that the kind of the x-ray detector system 50 is a flat panel for example. For example, the object 200 is the hilum of the left lung (the hilum near the heart) in the breast part.

For example, the imaging person prepares imaging condition combinations 1 to 4 illustrated in FIG. 4. Next, by means of the imaging person inputting values illustrated in the imaging condition combination 1 in FIG. 4 as the imaging condition combination 1 onto the operation panel 20, the obtaining unit 12 obtains the imaging condition combination 1. Likewise, the obtaining unit 12 obtains imaging condition combinations 2 to 4. In the case of the imaging condition combination 1, the tube current is small, and thus the small focal spot (which has a nominal focal spot value of 0.6 mm) is used for the x-ray tube 40. In the case of each of the imaging condition combinations 2 to 4, the tube current is large, and thus the large focal spot (which has a nominal focal spot value of 1.2 mm) is used for the x-ray tube 40. The imaging condition combination 2 makes it possible to obtain the image which has an equivalent EI value which is equivalent to the EI value obtainable under the imaging condition combination 1 because the imaging condition combination 2 has a tube voltage and a mAs value (which is the product of the tube current and the imaging time) which are the same as those in the imaging condition combination 1, and has a tube current which is two times larger than that of the imaging condition combination 1, and thus the imaging condition combination 2 has imaging time which is the half of that of the imaging condition combination 1. Imaging condition combination 3 makes it possible to obtain the image which has the equivalent EI value which is equivalent to the EI value obtainable under the imaging condition combination 1 by means of adjusting the imaging time although the tube current is 320 mA and the tube voltage is a maximum tube voltage which can be generated in the case of the tube current. In each of the imaging condition combinations 1 to 3, the SID is 200 cm and the SOD is 188 cm. The imaging condition combination 4 makes it possible to obtain the image which has the equivalent EI value which is equivalent to the EI value obtainable under the imaging condition combination 1 because the imaging condition combination 4 has a nominal focal spot value, a tube voltage, and a tube current which are the same as in those in the imaging condition combination 3 and has imaging time which is the half of that of the imaging condition combination 3, and has an SID and an SOD which are reduced to 140 cm and 128 cm, respectively from those in the imaging condition combination 3. As described above, each of the imaging condition combinations 1 to 4 is an imaging condition combination in the case where the image which has the equivalent EI value is obtained. The obtaining unit 12 receives the plurality of imaging condition combinations as such.

Next, the first correspondence relations in Step S12 are described with reference to FIG. 5.

FIG. 5 is a diagram illustrating examples of the first correspondence relations.

Each of the first correspondence relations is the relation between (i) an imaging condition combination of a nominal focal spot value, a tube voltage, and a tube current among the imaging condition combinations obtained by the obtaining unit 12 and (ii) values f1 and f2 in an approximate function of an MTF based on an x-ray tube effective focal spot value. For example, when the obtaining unit 12 obtains the imaging condition combination 3 illustrated in FIG. 4, the nominal focal spot value is 1.2 mm, the tube voltage is 100 kVp, and the tube current is 320 mA, and thus f1 is 1.5 and f2 is 2.1.

The values f1 and f2 in the approximate function of the MTF based on the x-ray tube effective focal spot value on the x-ray tube focal plane in the first correspondence relation are values predetermined for each imaging condition combination of the x-ray tube nominal focal spot value, the tube voltage, and the tube current, so that a function G (u1) which indicates the MTF based on the x-ray tube effective focal spot value on the x-ray tube focal plane approximates to a measured MTF based on an x-ray tube effective focal spot value for each imaging condition combination of the x-ray tube nominal focal spot value, the tube voltage, and the tube current in a spatial frequency u1 domain on the x-ray tube focal plane calculated by setting the magnification ratio M to be a value within a predetermined range and setting a spatial frequency u domain which has a spatial frequency on the object 200 plane to be a predetermined spatial frequency domain.

Here, the x-ray tube nominal focal spot value and the x-ray tube effective focal spot value are described. The x-ray tube nominal focal spot value is a standardized indication, and a focal spot value at the time of imaging is the x-ray tube effective focal spot value. This x-ray tube effective focal spot value changes slightly when a tube voltage or a tube current changes, which slightly changes an MTF to be generated based on the x-ray tube effective focal spot value. In view of this, the present invention generates and uses an approximate function of a measured MTF based on the x-ray tube effective focal spot value instead of calculating the x-ray tube effective focal spot value. However, it is extremely difficult to approximate, using a function, such a measured MTF to be generated based on the x-ray tube effective focal spot value. Thus, the present invention limits the range of a magnification ratio for use in imaging and also limits the spatial frequency domain desired to be compared between images on the object 200 plane so as to limit, to a predetermined range, the spatial frequency domain in which the function developed for indicating the MTF to be generated based on the x-ray tube effective focal spot value is approximated. In this way, the present invention performs precise approximation using a function within the spatial frequency domain in the predetermined range.

In an x-ray imaging technique performed daily for medical use, imaging is performed under a condition that a magnification ratio M depending on an SOD (distance a) and an SID (distance b) is within a range of approximately 1 to 1.4. Accordingly, the magnification ratio M is set to a value larger than 1 and smaller than 1.4 as the value within the predetermined range. Stated differently, the positions of the x-ray tube 40, the object 200, and the x-ray detector system 50 are set to positions at which the magnification ratio M becomes a value larger than 1 and smaller than 1.4. In this embodiment, the magnification ratio M is set to 1.064 or 1.094 for example.

It is known that human eyes have the highest MTF at approximately 1.5 cycles/mm. For this reason, the spatial frequency domain which has the spatial frequency u domain on the object 200 plane as the predetermined spatial frequency domain is assumed to be 0.5 to 1.5 cycles/mm for example.

The spatial frequency u1 on the x-ray tube focal plane is expressed by Expression 9 below using the spatial frequency u on the object 200 plane and the magnification ratio M.

$$u1 = \left(\frac{(M-1)}{M}\right)u \quad \text{(Expression 9)}$$

Thus, when the magnification ratio M is assumed to be larger than 1 and smaller than 1.4, and also the spatial frequency domain which has the spatial frequency u domain on the object 200 plane is assumed to be 0.5 to 1.5 cycles/mm, the spatial frequency domain which has the spatial frequency u1 domain on the x-ray tube focal plane is calculated to be 0 to 0.43 cycles/mm according to Expression 9. Accordingly, the values f1 and f2 are values adjusted so that the function G (u1) approximates to a measured MTF based on an x-ray tube effective focal spot value for each imaging condition combination of the x-ray tube nominal focal spot value, the tube voltage, and the tube current in the spatial frequency domain in which the spatial frequency u1 on the x-ray tube focal plane is lower than 0.43 cycles/mm.

In this way, the values f1 and f2 illustrated in FIG. 5 are determined in advance for each imaging condition combination of a nominal focal spot value, a tube voltage, and a tube current. For example, the storage unit 11 stores, as a database, first correspondence relations in each of which an imaging condition combination of a nominal focal spot value, a tube voltage, and a tube current is associated with values f1 and f2.

Next, the second correspondence relations in Step S13 are described with reference to FIG. 6.

FIG. 6 is a diagram illustrating examples of the second correspondence relations.

Each of the second correspondence relations is a relation between the kind of an x-ray detector system 50 among the imaging conditions obtained by the obtaining unit 12 and values S1 and S2 in an approximate function of an MTF based on the kind of an x-ray detector system 50 on the x-ray detector system 50 plane. FIG. 6 illustrates a flat panel and CRs as the kinds of the x-ray detector systems 50. For example, since the kind of the x-ray detector system 50 is the flat panel in FIG. 4, S1 is 0.085 and S2 is 2.

The values S1 and S2 in the approximate function of the MTF based on the kind of the x-ray detector system 50 on the x-ray detector system 50 plane in the second correspondence relation are values predetermined for each kind of the x-ray detector system 50, so that a function E (u2) which indicates the MTF based on the kind of an x-ray detector system 50 on the x-ray detector system 50 plane approximates to a measured MTF based on the kind of the x-ray detector system for each kind of the x-ray detector system 50 on the x-ray detector system 50 plane in a spatial frequency u2 domain on the x-ray detector system 50 plane calculated by setting the magnification ratio M to be a value within a predetermined range and setting a spatial frequency u domain which has a spatial frequency on the object 200 plane to be a predetermined spatial frequency domain.

It is extremely difficult to approximate, using a function, such a measured MTF to be generated based on the kind of the x-ray detector system. Thus, the present invention limits the range of a magnification ratio for use in imaging and also limits the spatial frequency domain desired to be compared between images on the object 200 plane so as to limit, to a predetermined range, the spatial frequency domain in which the function developed for indicating the MTF to be generated based on the kind of the x-ray detector system is approximated. In this way, the present invention performs precise approximation using a function within the spatial frequency domain in the predetermined range.

As described above, the magnification ratio M for use in imaging as the predetermined value is assumed to a value larger than 1 and smaller than 1.4, and the spatial frequency domain, as the predetermined spatial frequency domain, desired to be compared between images which has the spatial frequency u on the object 200 plane is assumed to be, for example, in a range from 0.5 to 1.5 cycles/mm.

The spatial frequency u2 on the x-ray detector system 50 plane is expressed by Expression 10 below using the spatial frequency u on the object 200 plane and the magnification ratio M.

$$u2 = \left(\frac{1}{M}\right)u \quad \text{(Expression 10)}$$

Thus, assuming that the spatial frequency domain which has the spatial frequency u on the object 200 plane is 0.5 to 1.5 cycles/mm, and also assuming that the magnification ratio M is larger than 1 and smaller than 1.4, the spatial frequency domain which has the spatial domain u2 on the x-ray detector system 50 plane is calculated to be 0.35 to 1.5 cycles/mm according to Expression 10. Accordingly, the values S1 and S2 are values adjusted so that the function E (u2) approximates to a measured MTF based on the kind of an x-ray detector system for each kind of the x-ray detector system 50 on the x-ray detector system 50 plane in the spatial frequency domain in which the spatial frequency u2 on an x-ray detector system 50 plane is 0.35 to 1.5 cycles/mm.

In this way, the values S1 and S2 illustrated in FIG. 6 are predetermined for each kind of an x-ray detector system 50. For example, the storage unit 11 stores, as a database, second correspondence relations between the kinds of an x-ray detector systems 50 and the values S1 and S2.

Next, a description is given of the amount of motion d of the object 200 in imaging time in Step S14.

The amount of motion d of the object 200 includes the amount of motion of the human body 100 in the object 200 on the object 200 plane (hereinafter simply referred to as the amount of motion of the human body 100) and the amount of motion made by an organ in the object 200 on the object 200 plane (hereinafter simply referred to as the amount of motion made by the organ). The object 200 plane includes the object 200, and is perpendicular to the incident direction of the x-ray. For example, even if the amount of motion of the human body 100 is 0, the object 200 moves due to the influence of the motion of the organ, and thus the amount of motion d includes the amount of motion made by the organ. The amount of motion d of the object 200 in the imaging time is determined based on a maximum amount of motion of the object 200 on the object 200 plane and time required for the amount of motion of the object 200 to reach the maximum amount of motion of the object 200. More specifically, the amount of motion d is determined based on (i) a maximum amount of motion of the human body 100 on the object 200 plane and a maximum amount of motion made by the organ, (ii) time required for the amount of motion of the human body 100 to reach the maximum amount of motion of the human body 100 and time required for the amount of motion made by the organ in the object 200 to reach the maximum amount of motion made by the organ, and (iii) the imaging time. More specifically, the amount of motion d is determined as below. It is assumed that the maximum amount of motion of the human body 100 is c (refer to FIG. 1), that the maximum amount of motion of the object 200 made by the organ is c2, and that the imaging time is in units of seconds.

When the time required for the amount of motion of the human body 100 to reach the maximum amount c of motion of the human body 100 is longer than the imaging time and the time required for the amount of motion made by the organ to reach the maximum amount of motion c2 made by the organ is longer than the imaging time, the amount of motion d of the object 200 is the amount of motion expressed as the product of the imaging time and the sum of the amount of motion of the human body 100 per second and the amount of motion made by the organ per second. The amount of motion d in this case is expressed by Expression 11 below.

$d=$((the amount of motion of human body 100 per second)+(the amount of motion made by organ per second))×(imaging time)  (Expression 11)

In addition, when the time required for the amount of motion of the human body 100 to reach the maximum amount of motion c of the human body 100 is longer than the imaging time and the time required for the amount of motion made by the organ to reach the maximum amount of motion c2 made by the organ is shorter than the imaging time, the amount of motion d of the object 200 is the amount of motion expressed as the sum of the product of the imaging time and the amount of motion of the human body 100 per second and the maximum amount of motion c2 made by the organ. The amount of motion d in this case is expressed by Expression 12 below.

$d=$(the amount of motion of human body 100 per second)×(imaging time)+c2  (Expression 12)

In addition, when the time required for the amount of motion of the human body 100 to reach the maximum amount of motion c of the human body 100 is shorter than the imaging time and the time required for the amount of motion made by the organ to reach the maximum amount of motion c2 made by the organ is longer than the imaging time, the amount of motion d of the object 200 is the amount of motion expressed as the sum of (i) the maximum amount of motion c of the human body 100 and (ii) the product of the imaging time and the amount of motion made by the organ per second. The amount of motion d in this case is expressed by Expression 13 below.

$d=c+$(the amount of motion made by organ per second)×(imaging time)  (Expression 13)

In addition, when the time required for the amount of motion of the human body 100 to reach the maximum amount of motion c of the human body 100 is shorter than the imaging time and the time required for the amount of motion made by the organ to reach the maximum amount of motion c2 made by the organ is shorter than the imaging time, the amount of motion d of the object 200 is the amount of motion expressed as the sum of the maximum amount of motion c of the human body 100 and the maximum amount of motion c2 made by the organ. The amount of motion d in this case is expressed by Expression 14 below.

$d=c+c2$  (Expression 14)

For example, it is assumed that the maximum amount of motion c of the human body 100 is 0 mm, and time required for the amount of motion of the human body 100 to reach the maximum amount of motion c of the human body 100 is 0 second. Furthermore, for example, it is assumed that the maximum amount of motion c2 made by an organ of the object 200 which is the hilum of the left lung in the breast part is 3 mm, and time required for the amount of motion made by the organ to reach the maximum amount of motion c2 made by the organ is 0.4 second. At this time, none of the imaging condition combinations 1 to 4 illustrated in FIG. 4 includes any imaging time that exceeds 0.4 second. Thus, the time required for the amount of motion of the human body 100 to reach the maximum amount of motion c of the human body 100 is shorter than the imaging time, and the time required for the amount of motion made by the organ to reach the maximum amount of motion c2 made by the organ is longer than the imaging time. Accordingly, the amount of motion d of the object 200 is calculated as the sum of (i) the maximum amount c (0 mm) of motion of the human body 100 and (ii) the product of the imaging time and the amount of motion made by the organ per second (3 mm/0.4 second).

Here, the third correspondence relations in Step S14 are described with reference to FIG. 7.

FIG. 7 is a diagram illustrating examples of the third correspondence relations.

For example, the operation panel 20 may receive a part (the kind of an object 200) in the human body 100. Furthermore, when the object 200 is a part around the stomach and intestines in the abdominal part, the operation panel 20 may receive information indicating the state(s) of the object(s) 200 such as the states of the stomach and intestines, for example, a normal state, a diarrhea state, and a state after intake of barium. In this way, by means of the imaging person inputting the kind(s) and state(s) of the object(s) 200 onto the operation panel 20, the maximum amount of motion c2 made by the organ and the time required for the amount of motion made by the organ to reach the maximum amount of motion c2 made by the organ are determined based on the corresponding one of the third correspondence relations illustrated in FIG. 7. In addition, for example, the operation panel 20 may receive a maximum amount of motion c of the human body 100 which has been measured by the imaging person and time required for the amount of motion of the human body 100 to reach the maximum amount of motion c of the human body 100. An amount of motion d is determined by comparing (i) the imaging time obtained by the obtaining unit 12 and (ii) the time required for the amount of motion of the human body 100 to reach the maximum amount of motion c of the human body 100 and the time required for the amount of motion made by the organ to reach the maximum amount of motion c2 made by the organ.

Each of the amounts of motion described above is converted into the amount of motion on the object 200 plane because the amount of motion in the direction perpendicular to the object 200 plane does not substantially affect the MTF.

It should be noted that the x-ray system 1 may include, for example, a motion detecting sensor which detects the maximum amount of motion c of the human body 100 and the time required for the amount of motion of the human body 100 to reach the maximum amount of motion c of the human body 100.

FIG. 8 illustrates the following determined in this way: the values f1 and f2 which are values in the approximate functions of the MTFs based on the x-ray tube effective focal spot values and also in the approximate functions of the total MTFs; the values S1 and S2 in the approximate functions of the MTFs based on the kind of the x-ray detector systems 50 and also in the approximate functions of the total MTFs; and the amounts of motion d of the object 200 in the approximate functions of the MTFs based on the amounts of motion of the object 200 and also in the approximate functions of the total MTFs. It is to be noted that FIG. 8 also illustrates magnification ratios M each of which is 1.064 or 1.094 as described above.

FIG. 8 is a diagram illustrating examples of values in approximate functions of total MTFs. As described in FIG. 8, values in an approximate function of a total MTF is determined for each of imaging condition combinations.

The computer 10 generates, for each imaging condition combination, an approximate function of the total MTF by substituting the magnification ratio M, the values f1 and f2, the amount of motion d, and the values S1 and S2 which have been obtained by the obtaining unit 12, and further generates total MTF simulation data. The total MTF simulation data is data expressed using a graph, numerical values, or the like for example. It is also good to generate an approximate function of a total MTF by multiplying: a function G (u) in which a magnification ratio M and values f1 and f2 are substituted; a function T (u) in which the amount of motion d is substituted; and a function E (u) in which a magnification ratio M and values S1 and S2 are substituted. Here, the total MTF simulation data is described with reference to the graph in FIG. 9.

Figure 9:
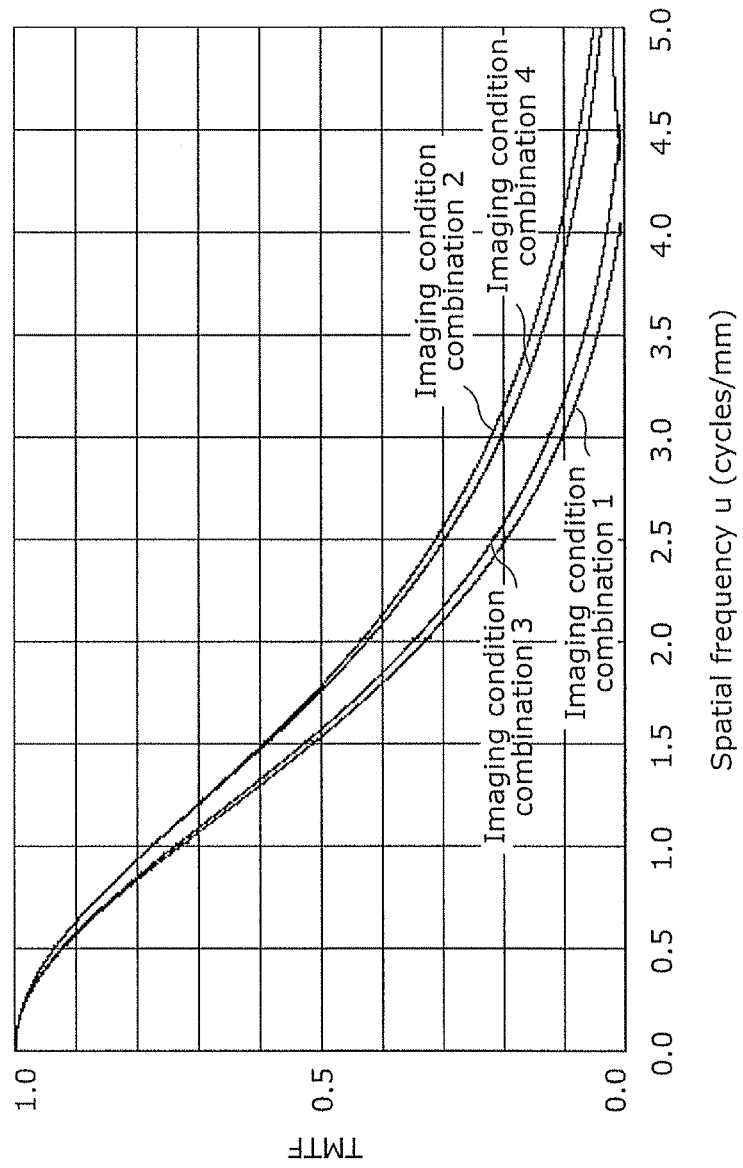
FIG. 9 is a graph illustrating examples of total MTF simulation data.

FIG. 9 is a graph illustrating examples of total MTF simulation data.

FIG. 9 is the graph showing approximate functions of total MTFs, in each of which the values in a corresponding one of the imaging condition combinations 1 to 4 illustrated in FIG. 8 are substituted. For example, the computer 10 compares the approximate functions of the total MTFs as shown in FIG. 9 in a spatial frequency u domain of 0.5 to 1.5 cycles/mm on the object 200 planes. After finding out that the total MTFs are higher in the following listed order of the imaging condition combinations 2, 4, 3, and 1, the computer 10 determines the imaging condition combination 2 as an imaging condition combination for achieving high resolution characteristics. In this way, the computer 10 can determine an imaging condition combination for achieving high resolution characteristics.

Advantageous Effects Etc.

The method for generating approximate functions of total MTFs of x-ray images according to this embodiment is a method for generating, based on conditions for imaging with an x-ray emitted by an x-ray tube, approximate functions of total MTFs indicating resolution characteristics of x-ray images of the object 200 which is a predetermined part of the human body 100 with a motion and is imaged using an x-ray emitted from the x-ray tube 40.

The method includes an obtaining step of obtaining: imaging condition combinations for the x-ray; the imaging condition combinations including a magnification ratio obtained by dividing a distance between an x-ray tube focal plane and an x-ray detector system 50 plane by a distance between the x-ray tube focal plane and an object 200 plane; an x-ray tube nominal focal spot value; a tube voltage; a tube current; imaging time; and a kind of an x-ray detector system 50, and conditions for the human body 100 at the time of imaging including: the kind of the object 200; the state of the object 200; the maximum amount of motion of the human body 100; and time required for the amount of motion of the human body 100 to reach the maximum amount of motion of the human body 100.

The method includes a first generating step of (i) generating an approximate function of an MTF based on an x-ray tube effective focal spot value on the x-ray tube focal plane by checking an imaging condition combination of the x-ray tube nominal focal spot value, the tube voltage, and the tube current among the imaging condition combinations obtained in the obtaining step, against a predefined first correspondence relation between the imaging condition combination of the x-ray tube nominal focal spot value, the tube voltage, and the tube current and values in the approximate function of the MTF based on the x-ray tube effective focal spot value, and (ii) converting, using the magnification ratio, the approximate function generated into an approximate function of an MTF based on the x-ray tube effective focal spot value on the object 200 plane.

The method includes a second generating step of (i) generating an approximate function of an MTF based on the kind of an x-ray detector system 50 on the x-ray detector system 50 plane by checking the kind of the x-ray detector system 50 among the imaging condition combinations obtained in the obtaining step, against a predefined second correspondence relation between the kind of the x-ray detector system 50 and values in the approximate function of the MTF based on the kind of the x-ray detector system 50 on the x-ray detector system plane, and (ii) converting, using the magnification ratio, the approximate function generated into an approximate function of an MTF based on the kind of the x-ray detector system 50 on the object 200 plane.

The method includes a third generating step of (i) generating an approximate function of an MTF based on an amount of motion of the object 200. The amount of motion of the object is determined by: (a) a maximum amount of motion made by an organ in the object, (b) time required for an amount of motion made by the organ to reach the maximum amount of motion made by the organ, (c) the imaging time, (d) the maximum amount of motion of the human body, and (e) the time required for the amount of motion of the human body to reach the maximum amount of motion of the human body. Here, (a) the maximum amount of motion made by an organ in the object and (b) the time required for an amount of motion made by the organ in the object to reach the maximum amount of motion made by the organ in the object are obtained by checking the kind of the object and the state of the object obtained in the obtaining step against a predefined third correspondence relation between (i) the kind of the object and the state of the object and (ii) the maximum amount of motion made by the organ in the object and the time required for the amount of motion made by the organ to reach the maximum amount of motion made by the organ.

The method includes a fourth generating step of generating an approximate function of a total MTF by multiplying the approximate function of the MTF based on the x-ray tube effective focal spot value on the object 200 plane, the approximate function of the MTF based on the kind of the x-ray detector system 50 on the object 200 plane, and the approximate function based on the amount of motion of the object 200 on the object 200 plane.

In addition, values in the approximate function of the MTF based on the x-ray tube effective focal spot value on the x-ray tube focal plane in the first correspondence relation are values predetermined for each imaging condition combination of the x-ray tube nominal focal spot value, the tube voltage, and the tube current, so that a function which indicates the MTF based on the x-ray tube effective focal spot value on the x-ray tube focal plane approximates to a measured MTF based on the x-ray tube effective focal spot value for each imaging condition combination of the x-ray tube nominal focal spot value, the tube voltage, and the tube current on the x-ray tube focal plane in a spatial frequency domain on the x-ray tube focal plane calculated by setting the magnification ratio to be a value within a predetermined range and setting a spatial frequency domain which has a spatial frequency on the object 200 plane to be a predetermined spatial frequency domain.

In addition, values in the approximate function of the MTF based on the kind of the x-ray detector system 50 on the x-ray detector system 50 plane in the second correspondence relation are values predetermined for each kind of the x-ray detector system 50, so that a function which indicates the MTF based on the kind of the x-ray detector system 50 on the x-ray detector system 50 plane approximates to a measured MTF based on the kind of the x-ray detector system 50 for each kind of the x-ray detector system 50 on the x-ray detector system 50 plane in a spatial frequency domain on the x-ray detector system 50 plane calculated by setting the magnification ratio to be a value within a predetermined range and setting a spatial frequency domain which has a spatial frequency on the object 200 plane to be a predetermined spatial frequency domain.

In addition, the amount of motion of the object 200 is an amount of motion expressed as a product of the imaging time and a sum of an amount of motion of the human body 100 per second and an amount of motion made by the organ per second when time required for the amount of motion of the human body 100 to reach a maximum amount of motion of the human body 100 is longer than the imaging time and time required for the amount of motion made by the organ to reach a maximum amount of motion made by the organ is longer than the imaging time.

In addition, the amount of motion of the object 200 is an amount of motion expressed as a sum of (i) a product of the imaging time and an amount of motion of the human body 100 per second and (ii) a maximum amount of motion made by the organ when time required for the amount of motion of the human body 100 to reach a maximum amount of motion of the human body 100 is longer than the imaging time and time required for the amount of motion made by the organ to reach a maximum amount of motion made by the organ is shorter than the imaging time.

In addition, the amount of motion of the object 200 is an amount of motion expressed as a sum of (i) a maximum amount of motion of the human body 100 and (ii) a product of the imaging time and an amount of motion made by the organ per second when time required for the amount of motion of the human body 100 to reach a maximum amount of motion of the human body 100 is shorter than the imaging time and time required for the amount of motion made by the organ to reach a maximum amount of motion made by the organ is longer than the imaging time.

In addition, the amount of motion of the object 200 is an amount of motion expressed as a sum of a maximum amount of motion of the human body 100 and a maximum amount of motion made by the organ when time required for the amount of motion of the human body 100 to reach a maximum amount of motion of the human body 100 is shorter than the imaging time and time required for the amount of motion made by the organ to reach a maximum amount of motion made by the organ is shorter than the imaging time.

It is to be noted that each of the amounts of motion described above is converted into the amount of motion on the object 200 plane.

In this way, the function indicating the total MTF in which the magnification ratio, the values in the approximate function of the MTF based on the x-ray tube effective focal spot value, the amount of motion of the object 200, and the values in the approximate function of the MTF based on the kind of the x-ray detector system 50 are substituted becomes the approximate function. Accordingly, it is possible to compare the differences in the resolution characteristics due to the differences in the imaging condition combinations easily (for example, accurately in a short period of time), based on, for example, total MTF simulation data which express the approximate function of the total MTF using a graph, numerical values, or the like.

It is to be noted that there is a need to limit the magnification ratio for use in imaging to a value in a predetermined range, and also limit the spatial frequency domain desired to be compared between images to a predetermined spatial frequency domain on the object 200 plane to generate, from a measured MTF, an approximate function that is partly accurate.

In addition, there is a need to prepare, in advance, the values f1 and f2 as illustrated in FIG. 5 for each imaging condition combination of the x-ray tube nominal focal spot value, the tube voltage, and the tube current by using the predetermined range of the magnification ratio, the predetermined spatial frequency domain on the object 200 plane, the measured MTF for each imaging condition combination of the x-ray tube nominal focal spot value, the tube voltage, and the tube current, and a function developed for indicating the MTF based on the x-ray tube effective focal spot value on the x-ray tube focal plane.

In addition, there is a need to prepare, in advance, the values S1 and S2 as illustrated in FIG. 6 for each kind of the x-ray detector system by using the predetermined range of the magnification ratio, the predetermined spatial frequency domain on the object 200 plane, the measured MTF for each kind of the x-ray detector system, and a function developed for indicating the MTF based on the kind of the x-ray detector system 50 on the x-ray detector system 50 plane.

In addition, there is a need to prepare, in advance, the magnification ratio within the predetermined value and the amount of motion of the object 200 to substitute in a function developed for indicating the MTF based on the amount of motion of the object 200 on the object 200 plane, taking into consideration that a motion made by an organ affects a motion of the object 200, based on the position of the object 200 and a motion of the human body 100.

In addition, a function G (u) of the MTF based on the x-ray tube effective focal spot value on the object 200 plane, a function T (u) of the MTF based on the amount of motion of the object 200 on the object 200 plane, a function E (u) of the MTF based on the kind of the x-ray detector system 50 on the object 200 plane, and a function TMTF (u) of the total MTF on the object 200 plane are expressed by Expressions 5, 3, 6, and 8 above where the values in the approximate function of the MTF based on the x-ray tube effective focal spot value are f1 and f2, the amount of motion of the object 200 is d, the values in the approximate function of the MTF based on the kind of the x-ray detector system 50 are S1 and S2, the magnification ratio is M, and the spatial frequency on the object 200 plane is a variable u.

In this way, it is possible to easily determine the magnification ratio M, the values f1 and f2, the amount of motion d, and the values S1 and S2, to thereby generate each of the approximate functions of the total MTFs based on the three major elements which cause blurs.

In addition, the values f1 and f2 in the approximate function of the MTF based on the x-ray tube effective focal spot value in the first correspondence relation are values predetermined for each imaging condition combination of the x-ray tube nominal focal spot value, the tube voltage, and the tube current, so that the function G (u1) (Expression 2) which is the function indicating the MTF based on the x-ray tube effective focal spot value approximates to the measured MTF based on the x-ray tube effective focal spot value for each imaging condition combination of the x-ray tube nominal focal spot value, the tube voltage, and the tube current in a spatial frequency domain which has a spatial frequency u1 ranging from 0 to 0.43 cycles/mm on the x-ray tube focal spot plane calculated by setting the magnification ratio M to be larger than 1 and smaller than 1.4 as the value within the predetermined range, and setting the spatial frequency domain to be a spatial frequency domain which has a spatial frequency ranging from 0.5 to 1.5 cycles/mm as the predetermined spatial frequency domain which has the spatial frequency u on the object 200 plane.

In addition, the values in the approximate function of the MTF based on the kind of the x-ray detector system 50 in the second correspondence relation are values predetermined for each kind of the x-ray detector system 50, so that the function E (u2) (Expression 4) which is the function indicating the MTF based on the kind of the x-ray detector system 50 on the x-ray detector system 50 plane approximates to the measured MTF based on the kind of the x-ray detector system 50 for each kind of the x-ray detector system 50 on the x-ray detector system 50 plane in the spatial frequency domain which has a spatial frequency u2 ranging from 0.35 to 1.5 cycles/mm on the x-ray detector system 50 plane calculated by setting the magnification ratio M to be larger than 1 and smaller than 1.4 as the value within the predetermined range, and setting the spatial frequency domain to be a spatial frequency domain which has a spatial frequency ranging from 0.5 to 1.5 cycles/mm as the predetermined spatial frequency domain which has the spatial frequency u on the object 200 plane.

In this way, the range of the magnification ratio M and the spatial frequency domain which has the spatial frequency u on the object plane are clearly determined, which makes it possible to accurately compare the differences in resolution characteristics due to differences in imaging condition combinations.

Other Embodiments

The method for generating, based on conditions for imaging with an x-ray emitted by an x-ray tube, approximate functions of total MTFs of x-ray images according to the present invention has been described above based on the embodiment above. However, the present invention is not limited to the above embodiment.

The present invention can be implemented not only as the computer 10 but also as a method including steps (processes) performed by the respective constituent steps of the computer 10.

For example, these steps may be executed by a computer. In addition, the present invention can be implemented as a program for causing the computer to execute the steps of the method. Furthermore, the present invention can be implemented as a non-transitory computer-readable recording medium such as a CD-ROM having the program recorded thereon.

Furthermore, the present invention covers embodiments which are obtainable by making various kinds of modifications that can be arrived at by any person skilled in the art to the embodiment and other embodiments, and embodiments which are implemented by combining any of the constituent elements and functions in the embodiment and other embodiments without deviating from the scope of the present invention.

The invention claimed is:

1. A method for generating an approximate function of a total modulation transfer function (MTF) of an x-ray image of an object, based on conditions for imaging with an x-ray emitted by an x-ray tube, the total MTF indicating a resolution characteristic of the x-ray image, the x-ray image being obtained by imaging the object which is a predetermined part of a human body with a motion, the method comprising:

an obtaining step of obtaining, via an obtaining unit of a computer comprising the obtaining unit, a first generating unit, a second generating unit, a third generating unit and a fourth generating unit, imaging condition combinations for the x-ray and conditions for the human body at a time of imaging, the imaging condition combinations including a magnification ratio obtained by dividing a distance between an x-ray tube focal plane and an x-ray detector system plane by a distance between the x-ray tube focal plane and an object plane, an x-ray tube nominal focal spot value, a tube voltage, a tube current, imaging time, and a kind of an x-ray detector system, the conditions for the human body including a kind of the object, a state of the object, a maximum amount of motion of the human body, and time required for an amount of motion of the human body to reach the maximum amount of motion of the human body;

a first generating step of (i) generating, via the first generating unit, an approximate function of an MTF based on an x-ray tube effective focal spot value on the x-ray tube focal plane by checking an imaging condition combination of the x-ray tube nominal focal spot value, the tube voltage, and the tube current among the imaging condition combinations obtained in the obtaining step, against a predefined first correspondence relation between the imaging condition combination of the x-ray tube nominal focal spot value, the tube voltage, and the tube current and values in the approximate function of the MTF based on the x-ray tube effective focal spot value on the x-ray tube focal plane, and (ii) converting, using the magnification ratio, the approximate function generated into an approximate function of an MTF based on the x-ray tube effective focal spot value on the object plane;

a second generating step of (i) generating, via the second generating unit, an approximate function of an MTF based on the kind of an x-ray detector system on the x-ray detector system plane by checking the kind of the x-ray detector system among the imaging condition combinations obtained in the obtaining step, against a predefined second correspondence relation between the kind of the x-ray detector system and values in the approximate function of the MTF based on the kind of the x-ray detector system on the x-ray detector system plane, and (ii) converting, using the magnification ratio, the approximate function generated into an approximate function of an MTF based on the kind of the x-ray detector system on the object plane;

a third generating step of generating, via the third generating unit, an approximate function of an MTF based on an amount of motion of the object, the amount of motion of the object being determined by: (a) a maximum amount of motion made by an organ in the object, (b) time required for an amount of motion made by the organ in the object to reach the maximum amount of motion made by the organ in the object, (c) the imaging time, (d) the maximum amount of motion of the human body, and (e) the time required for the amount of motion of the human body to reach the maximum amount of motion of the human body, (a) the maximum amount of motion made by an organ in the object and (b) the time required for an amount of motion made by the organ in the object to reach the maximum amount of motion made by the organ in the object being obtained by checking the kind of the object and the state of the object obtained in the obtaining step against a predefined third correspondence relation between (i) the kind of the object and the state of the object and (ii) the maximum amount of motion made by the organ in the object and the time required for the amount of motion made by the organ in the object to reach the maximum amount of motion made by the organ in the object; and a fourth generating step of generating, via the fourth generating unit, an approximate function of a total MTF by multiplying the approximate function of the MTF based on the x-ray tube effective focal spot value on the object plane, the approximate function of the MTF based on the kind of the x-ray detector system on the object plane, and the approximate function based on the amount of motion of the object on the object plane, wherein values in the approximate function of the MTF based on the x-ray tube effective focal spot value on the x-ray tube focal plane in the first correspondence relation are values predetermined for each imaging condition combination of the x-ray tube nominal focal spot value, the tube voltage, and the tube current, so that a function which indicates the MTF based on the x-ray tube effective focal spot value on the x-ray tube focal plane approximates to a measured MTF based on the x-ray tube effective focal spot value for each imaging condition combination of the x-ray tube nominal focal spot value, the tube voltage, and the tube current on the x-ray tube focal plane in a spatial frequency domain on the x-ray tube focal plane calculated by setting the magnification ratio to be a value within a predetermined range and setting a spatial frequency domain which has a spatial frequency on the object plane to be a predetermined spatial frequency domain, values in the approximate function of the MTF based on the kind of the x-ray detector system on the x-ray detector system plane in the second correspondence relation are values predetermined for each kind of the x-ray detector system, so that a function which indicates the MTF based on the kind of the x-ray detector system on the x-ray detector system plane approximates to a measured MTF for each kind of the x-ray detector system on the x-ray detector system plane in a spatial frequency domain on the x-ray detector system plane calculated by setting the magnification ratio to be a value within a predetermined range and setting a spatial frequency domain which has a spatial frequency on the object plane to be a predetermined spatial frequency domain, and the amount of motion of the object is:

an amount of motion expressed as a product of the imaging time and a sum of an amount of motion of the human body per second and an amount of motion made by the organ per second when time required for the amount of motion of the human body to reach a maximum amount of motion of the human body is longer than the imaging time and time required for the amount of motion made by the organ to reach a maximum amount of motion made by the organ is longer than the imaging time;

an amount of motion expressed as a sum of (i) a product of the imaging time and an amount of motion of the human body per second and (ii) a maximum amount of motion made by the organ when time required for the amount of motion of the human body to reach a maximum amount of motion of the human body is longer than the imaging time and time required for the amount of motion made by the organ to reach a maximum amount of motion made by the organ is shorter than the imaging time;

an amount of motion expressed as a sum of (i) a maximum amount of motion of the human body and (ii) a product of the imaging time and an amount of motion made by the organ per second when time required for the amount of motion of the human body to reach a maximum amount of motion of the human body is shorter than the imaging time and time required for the amount of motion made by the organ to reach a maximum amount of motion made by the organ is longer than the imaging time; and an amount of motion expressed as a sum of a maximum amount of motion of the human body and a maximum amount of motion made by the organ when time required for the amount of motion of the human body to reach a maximum amount of motion of the human body is shorter than the imaging time and time required for the amount of motion made by the organ to reach a maximum amount of motion made by the organ is shorter than the imaging time.

2. The method for generating an approximate function of a total MTF of an x-ray image, based on conditions for imaging with an x-ray emitted by an x-ray tube, according to claim 1, wherein a function G (u) of the MTF based on the x-ray tube effective focal spot value on the object plane, a function T (u) of the MTF based on the amount of motion of the object on the object plane, a function E (u) of the MTF based on the kind of the x-ray detector system on the object plane, and a function TMTF (u) of the total MTF on the object plane are expressed by Expressions 15 to 18 below where the values in the approximate function of the MTF based on the x-ray tube effective focal spot value are f1 and f2, the amount of motion of the object is d, the values in the approximate function of the MTF based on the kind of the x-ray detector system are S1 and S2, the magnification ratio is M, and the spatial frequency on the object plane is a variable u.

$$G(u) = \exp\left(-2\pi^2 \left(\frac{f1}{3}\right)^2 \left(\left(\frac{(M-1)}{M}\right)u\right)^{(f2)}\right) \quad \text{[Expression 15]}$$

$$T(u) = \frac{\sin(\pi u d)}{\pi u d} \quad \text{[Expression 16]}$$

$$E(u) = \frac{1}{1 + 4\pi^2 (S1)^2 \left(\frac{1}{M}u\right)^{(S2)}} \quad \text{[Expression 17]}$$

$$TMTF(u) = |G(u) \times T(u) \times E(u)|. \quad \text{[Expression 18]}$$

3. The method for generating an approximate function of a total MTF of an x-ray image, based on conditions for imaging with an x-ray emitted by an x-ray tube, according to claim 2, wherein the values in the approximate function of the MTF based on the x-ray tube effective focal spot value in the first correspondence relation are values predetermined for each imaging condition combination of the x-ray tube nominal focal spot value, the tube voltage, and the tube current, so that the function G (u1) which is the function indicating the MTF based on the x-ray tube effective focal spot value and expressed by Expression 19 below approximates to the measured MTF based on the x-ray tube effective focal spot value for each imaging condition combination of the x-ray tube nominal focal spot value, the tube voltage, and the tube current in a spatial frequency domain which has a spatial frequency (u1) ranging from 0 to 0.43 cycles/mm on the x-ray tube focal spot plane calculated by setting the magnification ratio M to be larger than 1 and smaller than 1.4 as the value within the predetermined range, and setting the spatial frequency domain to be a spatial frequency domain which has a spatial frequency ranging from 0.5 to 1.5 cycles/mm as the predetermined spatial frequency domain which has the spatial frequency u on the object plane, and the values in the approximate function of the MTF based on the kind of the x-ray detector system in the second correspondence relation are values predetermined for each kind of the x-ray detector system, so that the function E (u2) which is the function indicating the MTF based on the kind of the x-ray detector system on the x-ray detector system plane and expressed by Expression 20 below approximates to the measured MTF based on the kind of the x-ray detector system for each kind of the x-ray detector system in the spatial frequency domain which has a spatial frequency (u2) ranging from 0.35 to 1.5 cycles/mm on the x-ray detector system plane calculated by setting the magnification ratio M to be larger than 1 and smaller than 1.4 as the value within the predetermined range, and setting the spatial frequency domain to be a spatial frequency domain which has a spatial frequency ranging from 0.5 to 1.5 cycles/mm as the predetermined spatial frequency domain which has the spatial frequency u on the object plane.

$$G(u1) = \exp\left(-2\pi^2 \left(\frac{f1}{3}\right)^2 (u1)^{(f2)}\right) \quad \text{[Expression 19]}$$

$$E(u2) = \frac{1}{1 + 4\pi^2 (S1)^2 (u2)^{(S2)}}. \quad \text{[Expression 20]}$$

* * * * *